United States Patent [19]

Leveen

[11] 4,080,959

[45] Mar. 28, 1978

[54] METHOD FOR DETECTION OF TUMORS OF THE BREAST

[76] Inventor: Robert F. Leveen, 122 S. 51st St., Omaha, Nebr. 68132

[21] Appl. No.: 697,569

[22] Filed: Jun. 18, 1976

[51] Int. Cl.$^2$ .............................................. A61B 5/00
[52] U.S. Cl. .................................. 128/2 H; 128/404
[58] Field of Search .............. 128/2 H, 2 A, 2 R, 404; 73/356

[56] References Cited

U.S. PATENT DOCUMENTS

| | | | |
|---|---|---|---|
| 3,245,402 | 4/1966 | Barnes | 128/2 H |
| 3,335,716 | 8/1967 | Alt et al. | 128/2 H |
| 3,339,542 | 9/1967 | Howell | 128/2 H |
| 3,847,139 | 11/1974 | Flam | 128/2 H |

FOREIGN PATENT DOCUMENTS

| | | | |
|---|---|---|---|
| 2,356,183 | 10/1974 | Germany | 128/404 |

OTHER PUBLICATIONS

Brown, G. H., *Industrial Research*, May 1966, pp. 53–58.

*Primary Examiner*—Kyle L. Howell
*Attorney, Agent, or Firm*—Henry W. Foulds, Jr.

[57] ABSTRACT

A new method for detection of lesions and benign and malignant tumors of portions of the human body such as the female breast is described which comprises (a) coating the skin of that portion of the body which is to be evaluated for tumors with a heat sensitive color responsive chemical such as cholesterol (b) heating that portion of the body so coated with penetrating radiation such as diathermy in either the microwave or radio wave frequency and (c) scanning the color coated skin over that portion of the body so treated as to identify by color change that "hot spots" which indicate the location of possible tumors or lesions.

4 Claims, No Drawings

METHOD FOR DETECTION OF TUMORS OF THE BREAST

BACKGROUND OF THE INVENTION

Recent studies have shown that the inrease in the 5 year survival from breast cancer is closely associated with early detection of the tumor. This detection has been achieved primarily through screening of asymptomatic patients. The mass screening technique presently employed included clinical examination including palpation of the breast, mammography and thermography. The use of all three diagnostic modalities in concert yields a true positive detection rate of about 92 to 94% accuracy while the individual group positive rates vary from about 70 to 80%. The use of all three diagnostic techniques in tandem however is not without certain drawbacks both as regards the expense and time consumed in diagnosis and further has been recently pointed out to involve certain risks to the patient being diagnosed.

It has been alleged by several cancer experts that 5 years of mammograms with X-rays will eventually cause as many breast cancers as it detects and therefore represents an unjustifiable risk to the more than 300,000 women who will be participating in 27 breast cancer detection projects sponsored by the National Cancer Institute and various private groups across the nation.

Therefore it is now generally admitted that certain serious risks exist with the use of mammography in breast cancer detection and diagnosis. Alternatively the use of thermography alone has been considered since it has no associated irradiation and is relatively inexpensive. However it is not accurate and has a false positive rate as high as 40% in symptomatic patients and from 10 to 25% in asymptomatic patients. Thus for mass screening purposes both mammography and thermography demonstrate very substantial drawbacks and limitations.

OBJECTS OF THE INVENTION

It is a primary object of the present invention to describe a new method of modified thermography which lacks undesirable side effects and is a very accurate diagnostic indicator of tumor sites.

It is a concrete object of the present invention to describe a new color change technique for location of the potential or actual sites of breast tumors in females.

BRIEF DESCRIPTION OF THE INVENTION

A basic discovery on which this method of diagnosis is based is that "in vivo" tumor tissue has a blood flow which is approximately 1/20th that of the normal adjacent body tissue. When heated uniformly normal tissue dissipates its heat rapidly thru the vascular system which in effect acts as a radiator for the heat. In contrast the sluggish blood flow thru a tumor makes heat dissipation in this tissue negligble compared to normal tissue. In practice therefore it has been found that when breast tissue is heated with a diathermy device the normal breast tissue is able to dissipate the heat input as rapidly as it accumulates and hence there is no temperature change in normal breast tissue. This can be measured and indicated by a skin surface color indicator which would show a heat build up or lack of the same. However deep heat to the breast portion of the body as applied by diathermy to a tumor or lesion within the breast accumulates heat without an ability to dissipate the same and as a result the temperature in this spot rises significantly as reflected in a detectable difference in thermography related to a heat sensitive color indicator.

What this amounts to is fine tuned thermography based on color change in tissue which has been universally treated with radiofrequency or microwave frequency. This obviously increases the sensitivity of thermography to an appreciable extent. While it is true that a vascular cystic structure in the breast will also heat up in response to diathermy in much the same way that tumor tissue does and present a false positive response the proposed method of detection will significantly eliminate the false negative results and reduce the diagnosis to its simplest terms i.e. weeding out the cystic structure from the tumors. This obviates the inherent dangers of mammography in any event.

The diathermy device employed in the method is preferably an inductance coil having a radio frequency operable at a preferred frequency of 13.56 megahertz and a wattage ranging from 50 to about 150 watts or higher. This coil does not heat fatty tissue but does heat salt containing tissue substantially and will penetrate the body of the patient to a depth sufficient to contact and heat up the submerged tumors selectively to such a degree that the difference in heat retention is carried externally to the skin as manifest by a visible skin "hot spot." This phenomenon creates a superfically visible color area which corresponds in location to the invisible tumor or avascular cyst. Because the cholesterol coating is thermally responsive with color change the site of the abnormal submerged tissue mass is marked by the surface discoloration set apart from the reference color of the background area.

In conduct of my diagnosis the use of relatively long i.e. 20 to 22 meters in length, radiowaves is preferred because unlike microwaves they are not absorbed by the body fat tissue. In particular with tumors of the breast the fatty tissue is replaced by salt containing tumor tissue. This tissue can be differentially heated and distinguished from normal glandular tissue because the tumor tissue acts as a heat sink and goes to temperatures in the range of 104° to 118° F while the normal tissue at the highest will not exceed a temperature of 104° F and generally will only go to a temperature of 98.6° to 102° F during diagnosis.

While I prefer liquid crystals of cholesterol as my color change indicator it is of course clear that any chemical substance that will respond to heat changes in the underlying substrate by a color change sufficiently long to enable the clinical evaluator to spot and mark the location of the change for a follow up bioposy of the underlying tissue and/or a computerized body scan of the breast to determine the total picture may be employed to achieve the end result.

The following is an example of the preferred mode of practice of my invention as applied to the location based on scanning of a small malignant sarcoma of the left breast of a young woman:

EXAMPLE

A young woman who desires to have a diagnosis of both breasts has a thin coating of carbon black painted thereon. Immediately thereafter a thin 1-5 mil. coating of liquid crystals of cholesterol in an aqueous suspension is painted thereon and permitted to spread evenly over the surface of the breast including the nipples. A radiowave generator unit connected to several 5 inch diameter copper electrodes disc operatively connected thereto by a six foot shielded coaxial cable as more particularly described in pending U.S. Pat. application Ser. No. 595,095 filed July 11, 1975, of H. LeVeen, now U.S. Pat. No. 4,032,860, is brought into contact with the skin of the breast of the patient. This is done by positioning the one copper electrode disc over the face of the breast and the second copper disc placed on the back of the patient so that the entire breast lies in a pathway between the two discs. The generator is then turned on and sufficient radiowave energy at a frequency of 13.56 Megahertz transmitted to the breast area to elevate the temperature of the breast to a temperature ranging between 100° – 102° F for about 20 minutes. The skin temperature is measured by either alcohol thermometer needles or other known means of monitoring of the tissue temperature of the surface and deep fatty tissue of the breast at its center.

During the energy input time while the radiowave generator is turned on and the electrodes attached the areas of coated skin of the breast are observed for color variations and marked accordingly. By reference to a color chart for increased thermal aggregation or "hot spots" i.e. those sites where such color spots associated with high heat concentration occur can be easily detected.

For instance if the green color is related to the tissue temperature of normal tissue (100°–102° F) after 20 minutes of heating and a red color associated with tissue at a higher temperature of 115° – 120° F then the occurrence of a red spot skin spot in a surrounding green field will indicate the possible location of a tumor or hot tissue under the location of the skin spot. This spot can then be marked off for subsequent biopsy and confirmatory diagnosis.

If no off color spots turn up then the scan indicates the tissue of the entire breast is probably free of cancerous tumors or submerged lesions.

I claim as my invention:

1. A method for the detection of tumor sites in vivo in human tissue which comprises:
    (a) coating a portion of the skin tissue surface of the body with a thin film of a heat sensitive liquid which changes color in response to thermal energy input into the tissue
    (b) heating the entire portion of the body subadjacent to the coated tissue surface uniformly to elevate the normal tissue of the portion of the body heated to a temperature of not more than 104° F and the abnormal tissue of the same portion to a temperature in excess of this temperature so as to cause a color differential in the surface coating and
    (c) scanning the skin tissue so color coated to identify hot spots thereon as possible sites of underlying tumors 2. A method according to claim 1 wherein the portion of skin tissue is coated with liquid crystals of cholesterol which change color in response to temperature changes in the underlying substrate.

3. A method according to claim 1 wherein the portion of a body is heated by the application of diathermy.

4. A method according to claim 3 wherein the portion of the body treated is heated with diathermy for from 10 to 30 minutes at from 50 to 150 watts of input energy.

* * * * *